(12) United States Patent
Yomtov et al.

(10) Patent No.: US 10,695,477 B2
(45) Date of Patent: *Jun. 30, 2020

(54) HARD-WIRED IMPLANTED CONTROLLER SYSTEM

(71) Applicant: HeartWare, Inc., Miami Lakes, FL (US)

(72) Inventors: Barry M. Yomtov, Marblehead, MA (US); John Robert Batty, Jr., Miami, FL (US); Daniel Tamez, Plantation, FL (US)

(73) Assignee: HeartWare, Inc., Miami Lakes, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/123,446

(22) Filed: Sep. 6, 2018

(65) Prior Publication Data

US 2019/0001038 A1   Jan. 3, 2019

Related U.S. Application Data

(63) Continuation of application No. 14/640,718, filed on Mar. 6, 2015, now Pat. No. 10,092,684, which is a continuation of application No. 14/151,720, filed on Jan. 9, 2014, now Pat. No. 9,005,105, which is a continuation of application No. 12/886,369, filed on Sep. 20, 2010, now Pat. No. 8,628,460.

(Continued)

(51) Int. Cl.
| | |
|---|---|
| A61M 5/14 | (2006.01) |
| A61M 1/12 | (2006.01) |
| A61B 5/00 | (2006.01) |
| A61M 1/10 | (2006.01) |

(52) U.S. Cl.
CPC ............ *A61M 1/127* (2013.01); *A61B 5/0015* (2013.01); *A61M 1/1086* (2013.01); *A61M 1/12* (2013.01);
(Continued)

(58) Field of Classification Search
CPC ...... A61M 1/127; A61M 1/1086; A61M 1/12; A61M 2205/3592; A61M 2205/10; A61M 2205/3523; A61M 2205/18; A61B 5/0015
See application file for complete search history.

(56) References Cited

U.S. PATENT DOCUMENTS

| | | | |
|---|---|---|---|
| 2002/0016568 A1* | 2/2002 | Lebel ................. | A61N 1/37211 604/131 |
| 2005/0107658 A1 | 5/2005 | Brockway et al. | |

(Continued)

FOREIGN PATENT DOCUMENTS

| | | |
|---|---|---|
| WO | 0020051 A1 | 5/2000 |
| WO | 2007053881 A1 | 5/2007 |
| WO | 2011081626 A1 | 7/2011 |

OTHER PUBLICATIONS

International Search Report and Written Opinion dated Nov. 17, 2010 by the International Searching Authority (ISA/US) in connection with International Application No. PCT/US10/49666.

(Continued)

*Primary Examiner* — Amanda K Hulbert
*Assistant Examiner* — Natasha Patel
(74) *Attorney, Agent, or Firm* — Christopher & Weisberg, P.A.

(57) ABSTRACT

A circulatory assist system is disclosed, the system including an implantable electrical device having an electric motor, an implantable controller connected to the implantable electrical device, and an implantable power source connected to the controller for supplying power to the controller. The (Continued)

controller is attachable to a first side of a percutaneous connector. A second side of the percutaneous connector, opposite to the first side, allows external connectivity to said controller.

9 Claims, 3 Drawing Sheets

Related U.S. Application Data

(60) Provisional application No. 61/399,315, filed on Jul. 9, 2010, provisional application No. 61/277,135, filed on Sep. 21, 2009.

(52) U.S. Cl.
CPC ..... *A61M 2205/10* (2013.01); *A61M 2205/18* (2013.01); *A61M 2205/3523* (2013.01); *A61M 2205/3592* (2013.01)

(56) References Cited

U.S. PATENT DOCUMENTS

| | | |
|---|---|---|
| 2007/0142696 A1* | 6/2007 | Crosby ................. A61M 1/127 600/16 |
| 2009/0192749 A1 | 7/2009 | Morello et al. |
| 2009/0209945 A1* | 8/2009 | Lobl ................. A61M 5/14224 604/891.1 |
| 2011/0071336 A1 | 3/2011 | Yomtov et al. |
| 2011/0137108 A1 | 6/2011 | LaRose et al. |
| 2011/0160516 A1* | 6/2011 | Dague ................... A61M 1/127 600/16 |

OTHER PUBLICATIONS

International Preliminary Report on Patentability issued by the International Bureau of WIPO dated Mar. 27, 2012 in connection with International Application No. PCT/US2010/049666.
Extended European Search Report for Application No. 10818025.8 dated Jun. 11, 2014.

* cited by examiner

HARD-WIRED IMPLANTED CONTROLLER SYSTEM

CROSS-REFERENCE TO RELATED APPLICATIONS

This application is a continuation of U.S. patent application Ser. No. 14/640,718, filed Mar. 6, 2015, which application is a continuation of U.S. patent application Ser. No. 14/151,720, filed Jan. 9, 2014, now U.S. Pat. No. 9,005,105, which application is a continuation of U.S. patent application Ser. No. 12/886,369, filed Sep. 20, 2010, now U.S. Pat. No. 8,628,460, which is related to and claims priority from U.S. Patent Application Ser. No. 61/399,315, filed Jul. 9, 2010, and U.S. Patent Application Ser. No. 61/277,135, filed Sep. 21, 2009, all of which are incorporated herein by reference.

BACKGROUND OF THE INVENTION

This invention relates to implantable medical devices. Specifically, the invention relates to a system for controlling implantable medical devices.

Implantable medical devices such as ventricular assist devices are being developed for long term treatment of chronic heart failure. Such devices require a pumping mechanism to move blood. Due to the nature of the application, the pumping mechanism must be highly reliable. Patient comfort is also a significant consideration.

Transcutaneous energy transfer ("TET") systems are used to supply power to devices such as heart pumps implanted internally within a human body. An electromagnetic field generated by a transmitting coil outside the body can transmit power across a cutaneous (skin) barrier to a magnetic receiving coil implanted within the body. The receiving coil can then transfer the received power to the implanted heart pump or other internal device and to one or more batteries implanted within the body to charge the battery.

One of the challenges of such systems is insufficient battery lifetime. The implanted battery may be required to supply the implanted device's entire power demand for one to several hours at a time, such as when the patient does activities that preclude wearing the external TET power unit, such as showering or swimming. When the implanted battery is first implanted into the patient, the battery capacity is large and can meet the power demand for the required amount of time. However, when subjected to frequent charging and discharging, the implanted battery's capacity decreases. With decreased battery capacity, the patient cannot spend as much time without the external TET power unit. Eventually, the battery may need to be replaced so that the patient can go without the external TET power unit for long enough periods of time again.

In addition to the foregoing problems, the use of inductive coils by TET systems to wirelessly transfer power to an implanted battery results in slow recharging times, as inductive charging has lower efficiency and increased heating in comparison to direct contact. Thus, there is a need in the art for ventricular assist device ("VAD") technology that improves patient lifestyle during internal battery operation ("tether free") and reduces bulkiness of the external hardware during normal operation. Therefore, there is a need in the art for an implantable component design that solves the problems described above.

BRIEF SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In accordance with one embodiment of the invention, an implantable controller and implantable power source attach to an implantable electrical device, such as a VAD, for powering the implantable electrical device when tether-free operation is desired, for example. In another embodiment of the present invention, a second power source, which may be referred to herein as an external power source in embodiments where implantable elements are actually implanted, supplies power to the implanted system and recharges the implantable power source by direct contact through a percutaneous connector.

In one embodiment, a backup controller is provided and it may have a hard wire communication link, through a percutaneous connector, to directly communicate with the implanted controller and serve as a programming/monitoring/diagnostic device). A back-up controller, which may be referred to herein as an external backup controller in embodiments where implantable elements are actually implanted, may also be plugged into the percutaneous connector to control the implantable electrical device. In one embodiment, a monitoring circuit of the implantable power unit can be used to monitor a condition of the implantable power source. The monitoring circuit can transmit a transcutaneous telemetry signal which represents the monitored condition to transfer control of the implantable electrical device to the backup controller or to trigger an alarm to alert a patient that an external power source should be connected to the percutaneous connector. In another embodiment the transcutaneous telemetry signal represents the monitored condition of the implantable controller for use by a control circuit to activate the backup controller. In one embodiment the backup controller transmits signals to the implantable controller through the percutaneous connector to disable the implantable controller and override the pump drive signals that are normally outputted by the implantable controller. In one embodiment, a logic signal used to switch between implantable controller and backup controller may be CMOS compatible (3.3 or 5 Volts, for example), depending on the internal logic design.

One object of the invention is to provide VAD technology that improves a patient's lifestyle during tether free operation. Another object of the invention is to reduce the external hardware required during normal operation.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION

The embodiments described below provide an alternate configuration to the prior art implantable systems. In some of these embodiments power is provided by an external power source, including a battery, cigarette lighter adapter, AC adaptor or DC power source, through a percutaneous connector. This configuration may be used as an alternative to the TET power transfer disclosed in U.S. Provisional Application No. 61/191,595, assigned to the same assignee of the present application. In some embodiments the percutaneous connector includes extra pin connections to allow a backup controller to be connected in case the implantable controller were to fail.

In some embodiments, signals are transmitted by the backup controller to inhibit or block the implantable controller's drive circuits so that the backup controller's drive circuits tap into pump drive connections. When the implantable controller's drive MOSFETS are not disabled, the internal circuitry may sink the signal from the external motor drive and not properly drive the pump.

Figure 1:
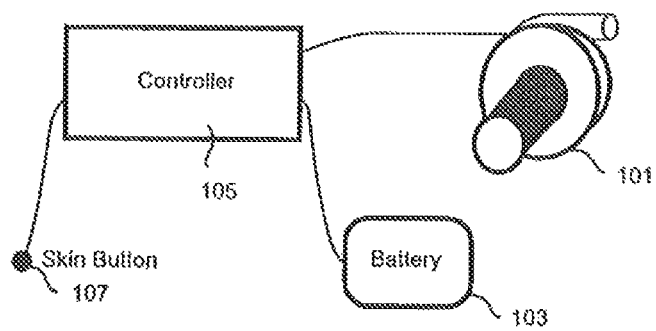
FIG. 1 illustrates components and operation of an implantable therapeutic electrical system in accordance with one embodiment of the invention.

FIG. 1 illustrates an embodiment of the present invention, including an implantable therapeutic electrical device 101, such as a VAD device, implantable power sources including a rechargeable power source 103, a controller 105, and a skin button 107. In the illustrated embodiment, the power source 103 supplies power to the controller 105. In turn, the controller 105 sends driving signals to a motor in the electrical device 101. The skin button 107 may be implemented as a percutaneous connector that allows external modules to connect to the implantable controller 105, as well as to the implantable power source 103 and implantable device 101 (through wire lines inside the controller). In one embodiment of the present invention, controller 105, power source 103 and device 101 are all implanted inside a patient's body.

In one embodiment DC power may be supplied through the skin button 107 to the controller 105, the power source 103 and the device 101. If the implantable device 101 is a VAD, its power demands may not be supplied by the implantable power source 103 for long periods of time. In such case, the implantable power source 103 may act as a supplemental power source, the primary power being supplied externally through skin button 107, but the implanted power source 103 may still be used to supply power for short periods of time.

Figure 2:
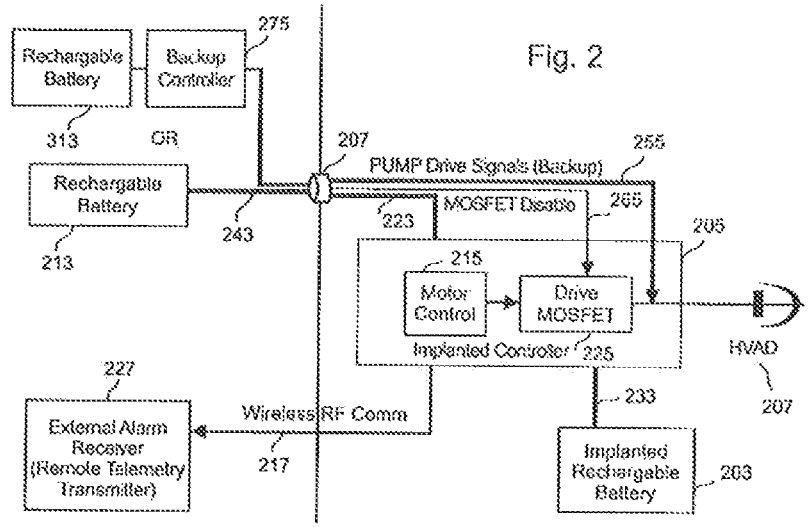
FIG. 2 illustrates a backup controller and a power source connected to an implantable therapeutic electrical system in accordance with one embodiment of the invention.

FIG. 2 illustrates another embodiment of the present invention. The figure illustrates implantable therapeutic electrical device 201, implantable power source 203, implantable controller 205, and wires 233, 255, 265 and 223. Also illustrated are external power source 213, external backup controller 235, external telemetry transceiver 227, as well as external wired connections 245 and 243 and wireless connection 217.

The controller 205 may include Drive MOSFETs 225 connected to a motor controller 215. The motor controller 215 may produce control signals for controlling a pump in the illustrated VAD 201. These control signals may be relayed to the VAD 201 by the Drive MOSFETs 225. The signals may also be conditioned by the Drive MOSFETs 225.

In one mode of operation, the Drive MOSFETs 225 operate as switches that interrupt the signal from the motor controller 215. In this mode of operation, the backup controller 235 sends the signal through wired connection 265 to command the interruption of the control signal from motor control 215. Also, the backup controller may supply a backup motor control signal 255 to drive the VAD 201. In one embodiment, this mode of operation is triggered after the remote telemetry transceiver 225 detects a signal sent over the wireless connection 217 indicative of a malfunction of motor controller 215. In another embodiment, the backup controller may receive the signal indicative of a malfunction through a wired connection.

In one embodiment of the present invention, the VAD's motor may be a permanent magnet brushless, sensorless DC motor. The motor is desirably highly reliable and maintenance free. The drive signals that are input to the stators(s) may be multiphase and biphasic to create a requisite rotating magnetic field excitation for normal operation of the motor. The stator drive signals may range from nearly zero volts to volts, and from zero to three (3) amps. Typical power dissipation may be between 1 to 45 Watts, depending upon selected RPM and resultant flow rate.

Also, the backup controller may have a hard wire communication link to directly communicate with the implanted controller and serve as a programming/monitoring/diagnostic device. The transceiver 225 may also detect other signals representative of measurements of operational parameters of the implanted module. These can be routed to the external controller 235 for remedial or corrective action. Examples of these parameters include low battery, excessive voltage applied to implanted electrical device (e.g., VAD), high temperature of implanted module, etc. When a signal indicative of low power is received, power may be supplied externally by power source 3131, the power signal being routed through backup controller.

Also, with reference to FIG. 2, in another mode of operation of the illustrated embodiment, the external rechargeable battery 213 is connected to the skin button 207 (instead of backup controller) and may supply power to the controller 205 through wired connections 223 and 243. The cable 223 may be of a lesser width and composition from the cable 243, as cable 223 is implantable. The skin button 207 serves not only as the percutaneous physical interface between external and internal modules, it also serves as the electrical interface.

The mode of operation where the external power source 213 supplies power to the controller 205 may be triggered by receipt by the transceiver 227 of a signal over wireless connection 217 which is indicative of implanted battery 203 having low power. The "low power" signal may be generated by monitoring the signal fed to the controller 205 over cable 233. The signal indicative of a malfunction (e.g., low power) may trigger a visual or audible alarm to alert the patient to connect external power source to the skin button.

Figure 3:
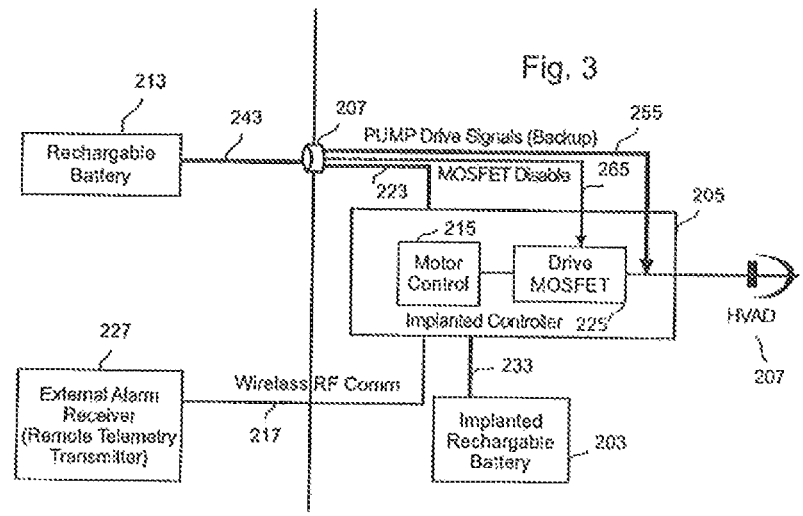
FIG. 3 illustrates a power source connected to an implantable therapeutic electrical system in accordance with one embodiment of the invention.

FIG. 3 illustrates another configuration of the system of the present invention. In the illustrated embodiment the backup controller 213 is not connected to the skin button 207. When the backup controller is not plugged into the skin button, the skin button may mechanically ground the input MOSFET disable signal 265 to avoid accidental disabling of controller 205.

In the embodiment illustrated in FIG. 3, the telemetry transceiver 227 may still detect whether the controller 205 functions properly and may activate a visual and/or audible alarm to alert the patient of any malfunctioning of the implanted controller 205. In one embodiment, the alarm may be inserted in a wristwatch for use by the patient.

Figure 4:
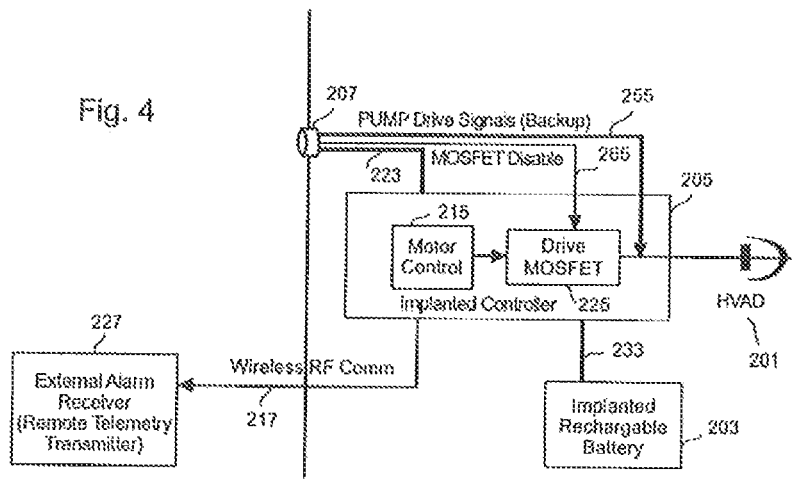
FIG. 4 illustrates an implantable therapeutic electrical system in accordance with one embodiment of the invention.

FIG. 4 illustrates the system components that may be used in one mode of operation. In this embodiment, neither the external battery (or power sources) 213 nor the backup controller is connected to the skin button 207, allowing the patient to move freely without any external physical connections.

Figure 5:
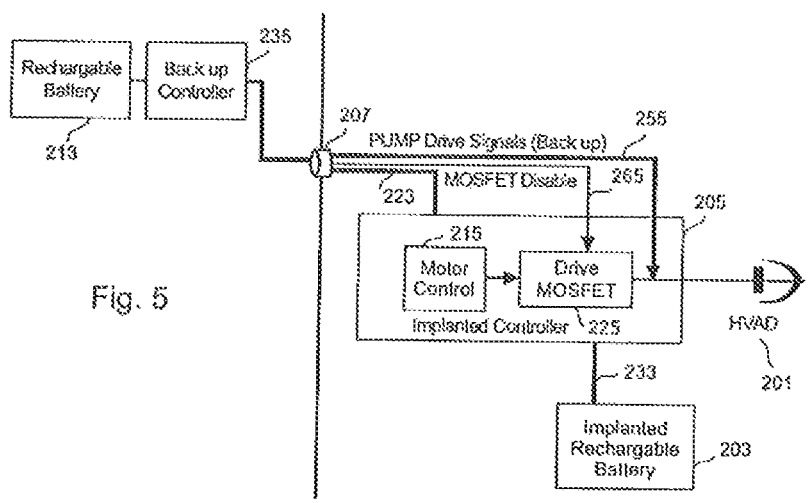
FIG. 5 illustrates a backup controller and a power source connected to an implanted therapeutic electrical system in accordance with one embodiment of the invention.

In the embodiment illustrated in FIG. 4, the external transceiver 227 is still able to detect anomalies in the operation of the implanted controller 205 or in the supply of power through cable 233 and alert the patient of these. In the event that there are any anomalies, the patient may plug in either the battery 213 or the backup controller 235 as illustrated in FIG. 3. Alternatively, the power source 213 and the controller 235 may be connected in series as illustrated in FIG. 5, with the signal for providing power being routed through the controller 235.

The foregoing description of possible implementations consistent with the present invention does not represent a comprehensive list of all such implementations or all variations of the implementations described. The description of only some implementation should not be construed as an intent to exclude other implementations. For example, an embodiment described as including implantable components should not be construed as an intent to exclude an implementation whereby those components are actually implanted in a patient's body. Artisans will understand how to implement the invention in many other ways, using equivalents and alternatives that do not depart from the scope of the following claims. Moreover, unless indicated to the contrary in the preceding description, none of the components described in the implementations are essential to the invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A circulatory assist system comprising:
an implantable electrical device;
an implantable power source operable to communicate with the implantable electrical device;
an implantable controller in communication with the implantable power source, the implantable controller including a monitoring circuit operable to monitor a condition of the implantable power source; and
a skin button in communication with the implantable controller, the skin button operable to mechanically ground at least one electrical signal of the implantable controller when the skin button is coupled to a patient, the at least one electrical signal including a disable signal.

2. The circulatory assist system of claim 1, wherein the monitoring circuit is operable to monitor power supplied by the implantable power source to the implantable controller.

3. The circulatory assist system of claim 1, wherein the monitoring circuit is operable to monitor an operation of the implantable controller.

4. The circulatory assist system of claim 1, further comprising a telemetry transmitter in communication with the monitoring circuit, the telemetry transmitter operable to transmit a transcutaneous telemetry signal associated with the condition of the implantable power source.

5. The circulatory assist system of claim 4, further comprising a backup controller in communication with the telemetry transmitter, the backup controller operable to receive the transcutaneous telemetry signal from the telemetry transmitter, and in response to receiving the transcutaneous telemetry signal, the backup controller being operable to communicate the disable signal to the implantable controller and assume control of the implantable electrical device.

6. The circulatory assist system of claim 5, wherein the implantable controller includes a drive MOSFET circuit, the drive MOSFET circuit including the disable signal.

7. The circulatory assist system of claim 1, further comprising:
a telemetry transmitter in communication with the monitoring circuit, the telemetry transmitter operable to transmit a transcutaneous telemetry signal associated with the condition of the implantable power source; and
a telemetry receiver in communication with the telemetry transmitter for receiving the transcutaneous telemetry signal from the telemetry transmitter, and in response to receiving the transcutaneous telemetry signal, the telemetry receiver being operable to activate an alarm.

8. The circulatory assist system of claim 7, further comprising a second power source, and the alarm alerting a patient to connect the second power source to the implantable electrical device.

9. The circulatory assist system of claim 8, further comprising a backup controller coupled to the second power source.

* * * * *